United States Patent [19]

Parry

[11] Patent Number: 4,813,940

[45] Date of Patent: Mar. 21, 1989

[54] INJECTION DEVICES

[75] Inventor: John S. Parry, Stroud, England

[73] Assignee: Sterimatic Holdings Limited, Tortola, British Virgin Isls.

[21] Appl. No.: 121,143

[22] Filed: Nov. 16, 1987

[30] Foreign Application Priority Data

Nov. 19, 1986 [GB] United Kingdom ............... 8627651
Apr. 1, 1987 [GB] United Kingdom ............... 8707755

[51] Int. Cl.$^4$ ............................................. A61M 5/32
[52] U.S. Cl. .................................... 604/198; 604/263
[58] Field of Search ................ 604/198, 192, 187, 263

[56] References Cited

U.S. PATENT DOCUMENTS 4,425,120  1/1984  Sampson et al. ................... 604/198
4,664,654  5/1987  Strauss .............................. 604/198
4,681,567  7/1987  Masters et al. .................... 604/198

Primary Examiner—John D. Yasko
Attorney, Agent, or Firm—Young & Thompson

[57] ABSTRACT

An accessory for an injection device of the kind in which liquid is drawn or expelled along a hollow needle comprises a protective sleeve for surrounding the needle. The sleeve has at least an end portion which is reciprocable in the direction of the length of the needle between an extended position in which the point of the needle is located within the sleeve to shield the point of the needle and a contracted position in which the point of thr needle projects from the sleeve, to enable an injection to be effected. A retaining arrangement is provided for retaining the sleeve in the extended position after the injection has been effected and for preventing the point of the needle from being exposed solely by application of pressure to the end portion of the sleeve in the direction of contracting movement.

13 Claims, 2 Drawing Sheets

INJECTION DEVICES

BACKGROUND OF THE INVENTION

This invention relates to injection devices, such as syringes, and accessories therefor.

After use of a syringe to perform an injection or take up a sample of blood from a patient, there is a risk that doctors or nurses will accidentally prick themselves with the needle of the syringe. This phenomenon is known as "needle stick", and can be highly dangerous due to the risk of transfer of blood-related diseases.

It is an object of the invention to provide an accessory for a syringe or other injection device which substantially eliminates the danger of needle stick.

SUMMARY OF THE INVENTION

According to the present invention there is provided an accessory for an injection device of the kind in which liquid is drawn or expelled along a hollow needle, the accessory comprising a protective sleeve for surrounding the needle and having at least an end portion which is reciprocable in the direction of the length of the needle between an extended position in which the point of the needle is located within the sleeve to shield the point of the needle and a contracted position in which the point of the needle projects from the sleeve, to enable an injection to be effected, and retaining means for retaining the sleeve in the extended position after the injection has been effected and preventing the point of the needle from being exposed solely by application of pressure to the end portion of the sleeve in the direction of contracting movement.

It is to be understood that the term "injection device" is used in this context to cover both a device for introducing a substance into a site penetrated by a needle and a device for taking up a substance, such as blood, from a site penetrated by a needle.

By use of such an accessory it is ensured that the point of the needle is protected after it has been used for performing an injection or taking up a sample of blood, and the danger of needle stick is thereby substantially removed. Even if pressure is accidentally applied to the end portion of the sleeve after it has been removed from the site of injection, this will not cause the point of the needle to be exposed by the sleeve.

BRIEF DESCRIPTION OF THE DRAWINGS

In order that the invention may be more fully understood, reference will now be made, by way of example, to the accompanying drawings, in which.

DETAILED DESCRIPTION OF THE DRAWINGS

Figure 1:
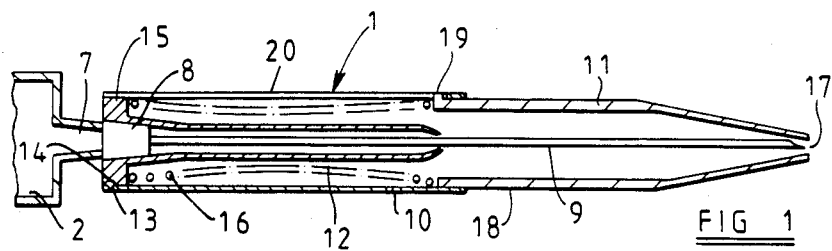
FIG. 1 is a longitudinal section through an accessory according to the invention, when in its extended position.

Referring to FIG. 1, an accessory in the form of an extendible sleeve 1 is shown fitted to one end of a syringe 2 comprising a hollow cylindrical barrel and a plunger (not shown) displaceable within the barrel. The syringe 2 has an outlet 7 at one end to which a hollow needle 9 is attached by means of an integral connector 8 which is a push fit on the outlet 7.

The extendible sleeve 1 comprises two telescoping sleeve parts 10 and 11, and an inner member 12. The sleeve part 10 surrounds the inner member 12 and is connected thereto by an annular rib 13 on the inside surface of the sleeve part 10 which engages by a snap action in an annular groove 14 in the outside surface of a base portion 15 of the inner member 12. The base portion 15 of the inner member 12 is a push fit on the needle connector 8.

The sleeve part 11 tapers towards its end furthest from the syringe 2 and has an aperture 17 at that end for passage of the point of the needle 9. The outside surface of the sleeve part 11 is formed with four equiangularly spaced longitudinal ribs 18 engaging the inside surface of the sleeve part 10 and at least one projection 19 engaging within a respective track 20 extending partially or completely through the wall of the sleeve part 10. Furthermore the sleeve 1 is resiliently biased towards its extended position by means of a compression spring 16 within the sleeve part 10 acting between the base portion 15 of the inner member 12 and the sleeve part 11. The spring 16 is a relatively weak spring which is reduced in diameter at an intermediate region along its length so that it has a small length when fully compressed.

The track 20 in the sleeve part 10 extends parallel to the needle 9 from the end of the sleeve part 10 adjacent the syringe 2 to a region a short distance from the opposite end of the sleeve part 10. Furthermore, as shown in the explanatory diagram of FIG. 3, the slot 20 is formed in that region with a retaining means in the form of a hooked portion 22 of the track 20 and an additional retaining means in the form of a shaped notch 21 in one side wall of the track 20.

In use of the syringe to perform an injection, the accessory 1 is fitted to the needle connector 8 after loading of the syringe 2 with injectate in conventional manner. The accessory 1 is initially in its extended position in which the point of the needle 9 is shielded by the sleeve part 11 as shown in FIG. 1. In this position the projection 19 on the sleeve part 11 is in the hooked portion 22 of the track 20 in the sleeve part 10, as shown at 19' in FIG. 3. The shape of the hooked portion 22 is such as to enable limited movement of the sleeve part 11 inwardly of the sleeve part 10 by application of pressure to the end of the sleeve part 11, but is such as to prevent inward movement of the sleeve part 11 to an extent to enable the point of the needle 9 to project from the aperture 17 at the end of the sleeve part 11.

Figure 3:
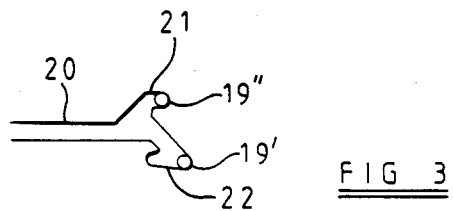
FIG. 3 is an explanatory diagram showing the shape of one end of a track provided in the accessory.

The sleeve part 11 is then twisted to release the projection 19 from the hooked portion 22 and to enable the projection 19 to enter the notch 21, as shown at 19" in FIG. 3, and to be retained therein by the biasing action of the spring 16. In the illustrated arrangement the accessory is thereby contracted to an extent to enable the point of the needle 9 to project through the aperture 17 in the end of the sleeve part 11 to a small extent. This then enables the point of the needle 9 to be accurately positioned at the intended site of injection. However, in a further non-illustrated arrangement, when the accessory is contracted in this manner, the point of the needle 9 still does not project through the end of the sleeve part 11.

In this partially contracted position, if the end of the sleeve part 11 is subjected to an accidental shock, the projection 19 will be caused to re-enter the hooked portion 22 under the action of the spring 16, thus again causing the point of the needle 9 to be shielded by the sleeve part 11 and retaining the accessory 1 in its extended position.

After location of the point of the needle 9 at the site of injection with the projection 19 retained in the notch 21, pressure is applied to the syringe 2 to cause the point of the needle 9 to enter the site of injection, and simultaneously the pressure applied to the end of the sleeve part 11 causes the sleeve part 11 to telescope within the sleeve part 10 against the action of the spring 16, resulting in movement of the projection 19 out of the notch 21 and along the straight portion of the track 20. The accessory 1 is shown in this contracted position in which the point of the needle 9 projects from the sleeve part 11 to a greater extent, in FIG. 2. The dose of injectate may then be delivered through the needle 9 in conventional manner.

When the dose has been delivered, the point of the needle 9 is withdrawn from the site of injection causing the sleeve part 11 to be returned to its extended position by the action of the spring 16, the projection 19 moving back along the straight portion of the track 20 and entering the hooked portion 22. Thus it will be appreciated that withdrawal of the point of the needle 9 from the patient automatically causes the accessory 1 to be returned to its secure position in which the point of the needle 9 is shielded by the sleeve part 11, and the point of the needle 9 cannot be subsequently exposed simply by application of pressure to the end of the sleeve part 11. Only by applying a positive twisting action to the sleeve part 11 can the point of the needle be subsequently re-exposed.

In certain applications, for example for use in a fitment for a multiple injection gun as described in the Applicants' U.S. Pat. No. 2,114,006, the notch 21 may be dispensed with. The retaining means constituted by the hooked portion 22 may also be of a different form to that described above. For example, it may take the form of a skirt on the outside of the sleeve part 11 which must be manually depressed to enable it to be overridden by the sleeve part 10 and allow contracting movement of the sleeve part 11.

Where the accessory is used for taking a blood sample, it may be necessary to detach the needle and protective sleeve from the syringe to enable the blood sample to be discharged to a container. To this end it may be advantageous for the outlet of the syringe to which the needle connector is connected to be formed with a weakened region which may be fractured to detach the needle and sleeve from the syringe. The arrangement should preferably be such that a fresh needle cannot be connected to the fractured syringe outlet.

The accessory may also be used with arrangements in which a syringe as such is not provided, such as the so-called Vacutainer (Registered Trade Mark) arrangement. In such an arrangement the needle is extended beyond the needle connector, the extension of the needle being covered by a rubber sleeve which is closed at its free end. After insertion of the point of the needle into the site of injection for the purpose of taking a blood sample, the extension of the needle, which is pointed at its end, is caused to puncture the rubber bung of a preevacuated container, the rubber sleeve being pushed back by this operation to enable the point of the extension to pass through the bung. The vacuum within the container then causes blood to be drawn from the site of injection into the container. It will be appreciated that an accessory of the type described above may be used not only to protect the injection end of the needle but also to protect the extension of the needle for insertion into the pre-evacuated container (in which case the rubber sleeve may be dispensed with).

Figure 2:
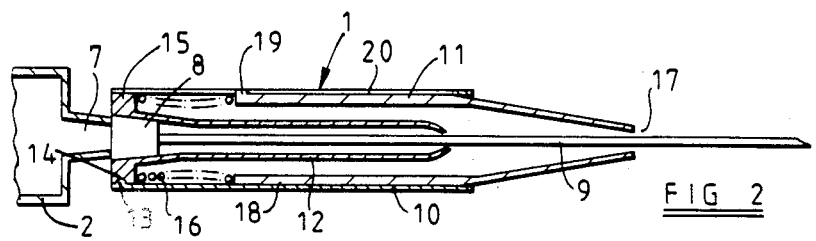
FIG. 2 is a longitudinal section through the accessory of FIG. 1, when in its fully contracted position.
Figure 4:
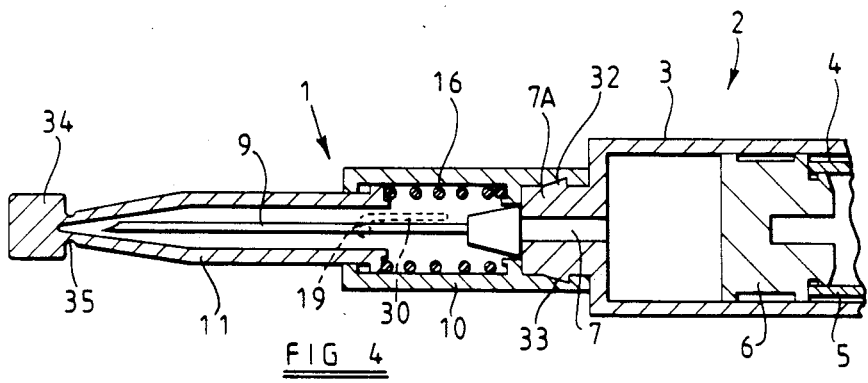
FIG. 4 is a longitudinal section through a further accessory according to the invention.
Figure 5:
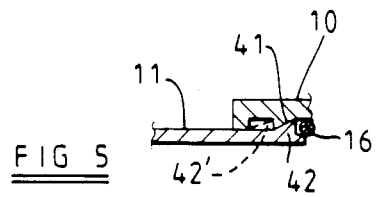
FIG. 5 is a scrap view illustrating a modification of the accessory of FIG. 4.

FIG. 4 shows another form of accessory in accordance with the invention, like parts being given the same reference numerals as in FIGS. 1 to 3. The extendible sleeve 1 is shown fitted to one end of a syringe 2 comprising a hollow cylindrical barrel 3 and a plunger 4 displaceable within the barrel 3. The plunger 4 comprises a hollow cylindrical shaft 5 and a piston part 6 made of resilient material and having a portion which is a force fit within the end of the shaft 5.

The sleeve part 10 is connectable to the connector 7A surrounding the outlet 7 of the syringe 2 by means of an annular rib 32 on the connector 7A which engages within an annular groove 33 in the inside surface of the sleeve part 10. It is preferred that the rib 32 and groove 33 have a section as shown so as to prevent subsequent detachment of the sleeve part 10 after attachment to the connector 7A. However, it is also feasible for the connection between these two parts to be by means of a screwthread of a bayonet fitting, optionally including a stop within the screwthread or fitting which is overridden on fitting of the sleeve to the connector, but which subsequently prevents the sleeve from being detached from the connector.

The sleeve part 11 has a tab portion 3 which is detachable from the end of the sleeve part 11, preferably by twisting, so as to cause the material of the end of the sleeve part 11 to rupture in the vicinity of an annular weakened region 3, thereby forming an aperture through which the point of the needle 9 may pass through the end of the sleeve part 11. In addition the sleeve 1 includes an arrangement for locking the sleeve in its extended position, this arrangement comprising a pin 19 projecting from the outside surface of the sleeve part 11 engaging within a hook-shaped track 3 in the inside surface of the sleeve part 10. The track 3 preferably does not extend completely through the wall of the sleeve part 10.

The above-described accessory is used in substantially similar manner to the accessory of FIGS. 1 to 3 to perform an injection. However the tab 3 must be detached from the end of the sleeve part 11 immediately prior to the injection being carried out, and the resulting apertured end of the sleeve part 11 is applied to the site of injection. The sleeve part 11 is then twisted to release the pin 19 from the hooked portion of the track 30, and simultaneously pressure is applied to the syringe to cause the sleeve part 11 to telescope within the sleeve part 10, thus causing the pin 19 to travel along the straight portion of the track 3 and the point of the needle 9 to pass through the apertured end of the sleeve part 11. On release of pressure applied to the sleeve part 11 after the dose has been delivered, the pin 19 moves back along the straight portion of the track 30 and enters the hooked portion to reassume its position as shown in FIG. 4 due to the slight rotational bias imparted to the sleeve part 11 by the spring 16 as the spring 16 becomes less compressed.

Where the syringe is to be used for taking a sample of blood from a patient, the blood sample may be taken up into the syringe in a substantially analogous manner to that described above in relation to delivery of injectate to a site of injection, except that the plunger 4 will of course be drawn in the direction away from the outlet 7 in this operation. After taking up of the blood sample, the sleeve will reassume its extended position and will again be locked in this position so that the danger of needle stick is substantially removed. In order to transfer the blood sample from the syringe to a storage container, the apertured end of the sleeve part 11 is applied to the top of the container, and the sleeve part is rotated to free the pin 19 from the hooked portion of the slot 20 whilst applying pressure to the syringe to cause the point of the needle 9 to pass through the apertured end of the sleeve part 11 and to puncture the top of the container. The blood sample may then be discharged through the needle 9 into the container in conventional manner, and again, on withdrawing the point of the needle, the sleeve will again reassume its extended position and will be locked in this position. The syringe is then disposed of with the sleeve still attached to protect the point of the needle.

Various modifications of the above described extendible sleeve accessory are contemplated within the scope of the invention. In one such modification, shown in FIG. 4A, the pin 19 and slot 20 are dispensed with, and instead the outside surface of the sleeve part 11 and the inside surface of the sleeve part 10 are provided with complementary locking formations 42 and 41. The locking formations 42 and 41 may be in the form of annular ribs or one or more projections which do not extend continuously around the periphery of the sleeve parts 10 and 11. Prior to introduction of the point of the needle into the site of injection, the relative positions of the formations 42 and 41 will be as shown in FIG. 4A, so that the sleeve 11 may be telescoped within the sleeve part 10 without requiring initial twisting of the sleeve part 11. However, when the sleeve 1 subsequently reassumes its extended position under the action of the spring 16, the formation 42 on the sleeve part 11 will be caused by the applied spring force to override the formation 41 so that the formation 42 will be moved to a position, as shown in broken lines at 42' in FIG. 4A, in which it engages behind the formation 41. It will be appreciated that this will result in the sleeve 1 being locked in its extended position. If the syringe is to be used only for injection purposes, the form of the interlocking formations may be such that such locking is permanent and cannot be overridden. However, where the syringe is to be used for taking up a sample of blood, it may be arranged that the sleeve part 11 may be subsequently telescoped within the sleeve part 10 by application of a relatively large force to the sleeve part 11 in the direction towards the syringe.

It is possible to arrange that, in any of the above described embodiments, once the sleeve has become locked in its extended position, it cannot subsequently be unlocked from this position. This can be achieved, for example, by providing a suitable click stop which can be overridden in one direction when the sleeve is moved into its locked position, but which cannot be overridden in the opposite direction in order to unlock the sleeve from this position. This would provide the additional advantage that the syringe could not be used for performing a subsequent injection, thereby obviating the risk of transfer of blood-related diseases from one user to another by use of the syringe to inject more than one patient.

Figure 6:
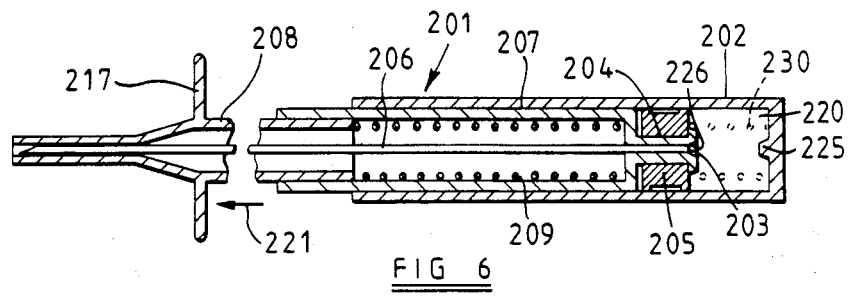
FIG. 6 is a longitudinal section through a further accessory according to the invention.
Figure 7:
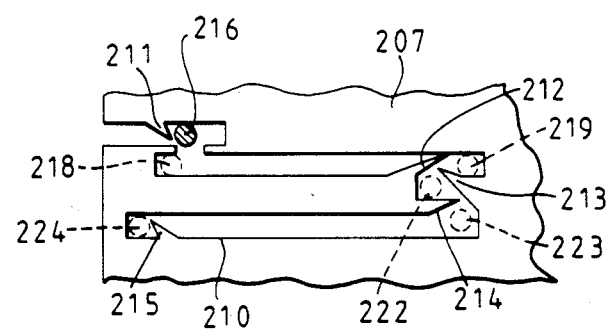
FIG. 7 is a developed view of a detail of the accessory of FIG. 6.

FIGS. 6 and 7 show a further form of accessory which is intended to remain permanently attached to the syringe 201 both during loading of the syringe with injectate and during injection. In this case the syringe 201 comprises a hollow cylindrical barrel 202 and a plunger piston 205 having an outlet 203. The outlet 203 is defined by a connector 204 to which a hollow needle 206 is permanently attached. A guide sleeve 207, whose function will become apparent from the description below, is also attached to the connector 204.

In order to protect the needle 206 and prevent the user from being accidentally pricked with the needle, a protective sleeve 208 surrounds the needle 206 and is biased into its extended position by a compression spring 209 within the guide sleeve 207. Furthermore the protective sleeve 208 is coupled to the guide sleeve 207 by a pin projecting outwardly from the sleeve 208 which engages within a guide track in the guide sleeve 207.

The manner in which the pin on the sleeve 208 engages within the guide track in the sleeve 207 will now be described with reference to the operation of the syringe and the developed view of the portion of the inner surface of the sleeve 207 in which the guide track 210 is provided. The sleeve 207 is made of nylon and incorporates fingers 211, 212, 213, 214 and 215 which allow movement of the pin 216 along the guide track 210 in one direction, but prevent movement of the pin 216 in the opposite direction. During initial assembly of the syringe the sleeves 207 and 208 are fitted together so that the pin 216 is moved into the guide track 210 and beyond the finger 211 to the position shown in solid lines in FIG. 7.

In operation of the syringe to perform an injection, the protective sleeve 208 is initially in its fully extended position, as shown in FIG. 6, in which it extends beyond the end of the needle 206, and the piston 205 is close to the closed end of the barrel 202. In order to uncover the tip of the needle 206 the protective sleeve 208 is manually grasped by means of a flange portion 217 thereon and is twisted relative to the barrel 202, whilst applying slight pressure to the flange 217 against the action of the spring 209, in order to release the pin 216 from the locked position shown in solid lines in FIG. 7. The pin 216 is thereby moved into the position 218 shown in broken lines. From this position the sleeve 208 may be moved inwardly of the barrel 202 to fully compress the spring 209 and to move the pin 216 past the finger 212 to the position 219. This movement exposes the tip of the needle 206 and at the same time causes the piston 205 to be moved to the end of the barrel 202 to expel air from the chamber 220.

The tip of the needle 206 may then be introduced into an injectate bottle and the sleeve 208 manually moved in the direction of the arrow 221 in FIG. 6. This causes the pin 216 in the guide track 210 to be moved beyond the finger 213 to the position 222 shown in FIG. 7. Further movement of the sleeve 208 in the direction of the arrow 221 causes the piston 205 to be drawn along the barrel 202 in the same direction in order to draw injectate along the needle 206 into the chamber 220. The syringe is held in this position prior to the injection being effected. Optionally a compression spring 230 may be provided within the chamber 220 so that the syringe is automatically filled with injectate when pressure is released from the sleeve 208.

The sleeve 208 is then again moved to compress the spring 209, firstly to expel any excess air from the chamber 220 and then, after insertion of the tip of the needle 206 into the injection site, in order to deliver the dose of injectate through the needle 206. Initial compression of the sleeve 208 causes movement of the pin 216 in the guide track 210 beyond the finger 214 to the position 223. Subsequent movement of the sleeve 208 in the same direction then causes movement of the piston 205 to expel air and subsequently injectate from the chamber 220. On completion of the injection the sleeve 208 is released to enable it to be moved into its fully extended position under the action of the spring 207, and the pin 216 is thereby moved in the guide track 210 beyond the finger 215 to the position 224 in which the sleeve 208 is locked in its extended position. In this position the sleeve 208 is locked in position relative to the sleeve 207 and hence also to the piston 205, although it is still possible for the piston 205 to be moved within the barrel 202 by moving the sleeve 208. Nevertheless such movement cannot be used to draw injectate into the chamber 220 by way of the needle 206 since the needle 206 is permanently covered by the sleeve 208.

In order to prevent the chamber 220 being subsequently filled with injectate by forcing injectate through the needle 206 under pressure, a pressure fill stop pipe 225 is located on the inner end wall of the barrel 202 for engaging a seating 226 on the opposite wall of the piston 205 when the piston 205 is in its endmost position. When the pip 225 engages the seating 226 injectate forced along the needle 206 will be prevented from entering the chamber 220.

Several modifications of the above-described syringe are possible within the scope of the invention. The connection between the piston 205 and the guide sleeve 207 by way of the connector 204 may either enable relative rotation between the sleeve 207 and the piston 205 or may prevent such rotation. If desired, fingers may be provided on the free end of the protective sleeve 208 extending radially outwardly relative to the needle 206 and shaped to fit around the injectate bottle as an aid to filling of the syringe with injectate. Furthermore the number and extent of the forward and backward movements of the sleeve 208 required in an injection cycle can be varied depending on the intended use and method of operation of the syringe.

I claim:

1. An accessory for an injection device of the kind in which liquid is drawn or expelled along a hollow needle, the accessory comprising a protective sleeve for surrounding the needle and having at least an end portion which is reciprocable in the direction of the length of the needle between an extended position in which the point of the needle is located within the sleeve to shield the point of the needle and a contracted position in which the point of the needle projects from the sleeve, to enable an injection to be effected, retaining means for retaining the sleeve in the extended position after the injection has been effected and preventing the point of the needle from being exposed solely by application of pressure to the end portion of the sleeve in the direction of contracting movement, and biasing means for resiliently biasing the sleeve towards its extended position, so that the sleeve will automatically assume its extended position shielding the point of the needle, and be retained therein by the retaining means, on release of pressure applied to the end portion of the sleeve in the direction of contracting movement, the sleeve comprising two parts which are reciprocable relative to one another in the direction of the length of the needle, one of the parts being adapted for attachment to the injection device and the other part having a portion through which the point of the needle may project in the contracted position, wherein a projection on one part engages within an enclosed track in the other part such that the projection is not accessible from outside the sleeve and such that relative movement of the projection within the track between an unlocked position and a locked position occurs as the sleeve moves from its contracted position to its extended position, and wherein the retaining means comprises a portion of said track within which said projection is held in the locked position.

2. An accessory according to claim 1, wherein additional retaining means are provided for retaining the sleeve in a partially contracted position, the additional retaining means comprising a further portion of said track within which said projection is held in a temporary retaining position.

3. An accessory according to claim 1, wherein the retaining means comprises resilient finger means in said track adapted to deflect to permit passage of said projection into the locked position and to subsequently engage behind said projection to prevent movement of said projection out of the locked position.

4. An accessory according to claim 1, wherein the retaining means comprises a hooked portion of said track within which said projection is held in the locked position.

5. An accessory according to claim 1, wherein said track includes a first elongate portion along which the projection travels when the sleeve moves from its initial extended position to its contracted position to enable an injection to be effected, and a second elongate portion along which the projection travels after the injection has been effected when the sleeve subsequently moves from its contracted position to its final extended position in which it is retained by the retaining means.

6. An accessory according to claim 1, wherein said one part is coupled to a movable piston of the injection device and is movable with the piston to draw liquid into, and expel liquid from, the injection device.

7. An accessory according to claim 1, wherein a hollow needle is permanently connected to the accessory so as to be surrounded by the sleeve.

8. An accessory according to claim 5, wherein said track includes resilient finger means located at the junction of the first and second elongate portions and adapted to deflect to permit passage of said projection from the first elongate portion to the second elongate portion and to subsequently adopt a position to prevent movement of said projection back to the first elongate portion.

9. An accessory for an injection device of the kind in which liquid is drawn or expelled along a hollow needle, the accessory comprising a protective sleeve for surrounding the needle and having at least an end portion which is reciprocable in the direction of the length of the needle between an extended position in which the point of the needle is located within the sleeve to shield the point of the needle and a contracted position in which the point of the needle projects from the sleeve, to enable an injection to be effected, and retaining means for retaining the sleeve in the extended position after the injection has been effected and preventing the point of the needle from being exposed solely by application of pressure to the end portion of the sleeve in the direction of contracting movement, the sleeve comprising two parts which are reciprocable relative to one another in the direction of the length of the needle, one of the parts being adapted for attachment to the injection device and the other part having a portion through which the point of the needle may project in the contracted position, wherein a projection on one part engages within a track in the other part, whereby relative movement of the projection within the track between an unlocked position and a locked position occurs as the sleeve moves from its contracted position to its extended position, said track including a first elongate portion along which the projection travels when the sleeve moves from its initial extended position to its contracted position to enable an injection to be effected, and a second elongate portion along which the projection travels after the injection has been effected when the sleeve subsequently moves from its contracted position to its final extended position in which it is retained by the retaining means.

10. An accessory according to claim 9, wherein the sleeve is resiliently biased towards its extended position, so that the sleeve will automatically assume its extended position shielding the point of the needle on release of pressure applied to the end portion of the sleeve in the direction of contracting movement.

11. An accessory according to claim 9, further comprising additional retaining means for retaining the sleeve in a partially contracted position.

12. An accessory for an injection device of the kind in which liquid is drawn or expelled along a hollow needle, the accessory comprising a protective sleeve for surrounding the needle and having at least an end portion which is reciprocable in the direction of the length of the needle between an extended position in which the point of the needle is located within the sleeve to shield the point of the needle and a contracted position in which the point of the needle projects from the sleeve, to enable an injection to be effected, and retaining means for retaining the sleeve in the extended position after the injection has been effected and preventing the point of the needle from being exposed solely by application of pressure to the end portion of the sleeve in the direction of contracting movement, the sleeve comprising two parts which are reciprocable relative to one another in the direction of the length of the needle, one of the parts being adapted for attachment to the injection device and the other part having a portion through which the point of the needle may project in the contracted position, wherein said one part is coupled to a movable piston to draw liquid into, and expel liquid from, the injection device.

13. An accessory according to claim 12, wherein a projection on one part engages within a track in the other part, whereby relative movement of the projection within the track between an unlocked position and a locked position occurs as the sleeve moves from its contracted position to its extended position.

* * * * *